United States Patent
Galeev et al.

(10) Patent No.: US 11,478,189 B2
(45) Date of Patent: Oct. 25, 2022

(54) SYSTEMS AND METHODS FOR RESPIRATORY ANALYSIS

(71) Applicant: BEIJING SHUNYUAN KAIHUA TECHNOLOGY LIMITED, Haidian District Beijing (CN)

(72) Inventors: Artem Galeev, Vancouver (CA); Yan Vule, Vancouver (CA); Aanchan Mohan, Vancouver (CA)

(73) Assignee: BEIJING SHUNYUAN KAIHUA TECHNOLOGY LIMITED, Beijing (CN)

( * ) Notice: Subject to any disclaimer, the term of this patent is extended or adjusted under 35 U.S.C. 154(b) by 422 days.

(21) Appl. No.: 15/914,857

(22) Filed: Mar. 7, 2018

(65) Prior Publication Data
US 2018/0256096 A1     Sep. 13, 2018

Related U.S. Application Data

(60) Provisional application No. 62/468,173, filed on Mar. 7, 2017.

(51) Int. Cl.
*A61B 5/00* (2006.01)
*A61B 5/0205* (2006.01)
(Continued)

(52) U.S. Cl.
CPC .......... *A61B 5/4818* (2013.01); *A61B 5/0205* (2013.01); *A61B 5/0816* (2013.01);
(Continued)

(58) Field of Classification Search
None
See application file for complete search history.

(56) References Cited

U.S. PATENT DOCUMENTS

| 5,280,791 A * | 1/1994 | Lavie ................... A61B 5/1103 600/509 |
| 2005/0217674 A1* | 10/2005 | Burton ................... A61B 5/145 128/204.23 |

(Continued)

FOREIGN PATENT DOCUMENTS

WO    WO2018081778    * 10/2017    .............. A61B 5/08

OTHER PUBLICATIONS

Foerster, F., M. Smeja, and J. Fahrenberg. "Detection of posture and motion by accelerometry: a validation study in ambulatory monitoring." Computers in Human Behavior 15.5 (1999): 571-583. (Year: 1999).*

(Continued)

*Primary Examiner* — Jacqueline Cheng
*Assistant Examiner* — Jairo H Portillo
(74) *Attorney, Agent, or Firm* — Young Basile Hanlon & MacFarlane, P.C.

(57) ABSTRACT

Examples described herein include systems and methods for determining sleep characteristics based on movement data. In one example, a device including at least one accelerometer can be worn by a user during the night. The accelerometer can be configured to detect small motions of the user and provide an output signal. The output signal can be filtered and used to determine whether the user was sleeping during a particular timeframe. The output signal can also be used to determine a sleep characteristic of the sleep, such as light sleep, deep sleep, REM sleep, obstructive apnea, or central apnea.

20 Claims, 8 Drawing Sheets

(51) Int. Cl.
*A61B 5/113* (2006.01)
*A61B 5/08* (2006.01)
*A61B 5/11* (2006.01)

(52) U.S. Cl.
CPC ............ *A61B 5/113* (2013.01); *A61B 5/1123* (2013.01); *A61B 5/4812* (2013.01); *A61B 5/7203* (2013.01); *A61B 5/725* (2013.01); *A61B 5/1112* (2013.01); *A61B 5/681* (2013.01); *A61B 5/6802* (2013.01); *A61B 5/7282* (2013.01); *A61B 2562/0219* (2013.01)

(56) References Cited

U.S. PATENT DOCUMENTS

| | | | | |
|---|---|---|---|---|
| 2006/0241446 | A1* | 10/2006 | White | G01S 15/8956 600/443 |
| 2008/0015457 | A1* | 1/2008 | Silva | A61B 5/113 600/534 |
| 2009/0281433 | A1* | 11/2009 | Saadat | A61B 5/68335 600/483 |
| 2010/0016682 | A1* | 1/2010 | Schluess | A61B 5/08 600/301 |
| 2010/0204586 | A1* | 8/2010 | Pu | A61B 5/4818 600/484 |
| 2011/0105915 | A1* | 5/2011 | Bauer | A61B 5/0456 600/484 |
| 2012/0313773 | A1* | 12/2012 | Loree, IV | A61B 5/681 340/522 |
| 2013/0072763 | A1* | 3/2013 | Shtalryd | A61B 5/01 600/534 |
| 2013/0234823 | A1* | 9/2013 | Kahn | G05B 13/00 340/3.1 |
| 2014/0135631 | A1* | 5/2014 | Brumback | A61B 5/11 600/479 |
| 2014/0275824 | A1* | 9/2014 | Couse | A61B 5/0024 600/301 |
| 2014/0364770 | A1* | 12/2014 | Slonneger | A61B 5/4812 600/595 |
| 2015/0250418 | A1* | 9/2015 | Ashby | A61B 5/02433 600/474 |
| 2015/0374292 | A1* | 12/2015 | Wyeth | A61B 5/721 600/409 |
| 2016/0007934 | A1* | 1/2016 | Arnold | A61B 5/1123 600/595 |
| 2016/0094899 | A1* | 3/2016 | Aumer | A61B 5/6802 340/870.07 |
| 2016/0242654 | A1* | 8/2016 | Quinlan | G16H 20/40 |
| 2018/0177464 | A1* | 6/2018 | DeBusschere | A61B 5/0077 |

OTHER PUBLICATIONS

Zhou, Shengli, et al. "Real-time hand-writing tracking and recognition by integrated micro motion and vision sensors platform." 2012 IEEE International Conference on Robotics and Biomimetics (Robio). IEEE, 2012. (Year: 2012).*

* cited by examiner

Rear view

Side view

Front view

Fig. 4A Example of raw data

SYSTEMS AND METHODS FOR RESPIRATORY ANALYSIS

PRIORITY CLAIM

This application claims priority to U.S. Provisional Patent Application No. 62/468,173, entitled "SYSTEMS AND METHODS FOR RESPIRATORY ANALYSIS" and filed Mar. 7, 2017, which is hereby incorporated herein in its entirety.

FIELD OF THE DISCLOSURE

The embodiments relate generally to systems and methods that use data collected by a wearable device to calculate, among other things, respiratory signals and rates, as well as a variety of respiratory events including, but not limited to, sleep apnea events and respiratory failures.

BACKGROUND

Respiration rate can provide important information regarding a person's health. Respiration information can also be used to assess the quality of a person's sleep. Abnormal respiratory events can be used to predict the onset of illnesses or other serious conditions. Abnormal respiratory events that occur during sleep can be indicative of other health issues, such as sleep apnea.

There are a number of "contact" respiration rate monitoring systems available today. As used herein, "contact" systems include systems comprising a device or instrument that makes physical contact with a person in order to collect respiratory information. Examples of contact systems available today can measure respiratory sounds, respiratory air flow, respiratory related chest or abdominal events, respiratory CO2 emission and oximetry probe SpO2. Respiration information can also be derived from other collected information, such as from a electrocardiogram (ECG).

However, the contact systems available today can be cumbersome for a subject to wear and can disrupt a person's lifestyle or ability to sleep comfortably. The equipment used in these systems can also be expensive and impractical for monitoring respiration on a daily basis, particularly that of a healthy person. Trained physicians and other medical personnel are often needed to assess the information collected before any useful information or insights can be provided to the subject.

Thus, a need exists for improved systems, devices, and techniques for determining, among other things, a user's respiration rate and the presence of various respiratory events. Moreover, improved systems, devices, and techniques are needed to ensure the accuracy, reliability, and comfort of systems configured to collecting such information.

SUMMARY OF THE DISCLOSURE

In accordance with certain embodiments of the present disclosure, components and processes used in devices and systems that collect respiratory signals and assess a subject's respiratory rate or the occurrence of a respiratory event are disclosed. In some embodiments, the monitoring devices may be a wrist watch, bracelet, or arm band comprising one or more components. The monitoring devices may comprise one or more accelerometers, including but not limited to one or more three-axis accelerometers. In such embodiments, acceleration data collected by the accelerometer may be used to determine a subject's respiratory signal, respiratory rate, and/or the instance of a respiratory event. As used herein, an "event" is intended to describe a respiratory abnormality, such as a respiratory signal that varies significantly from a normal or health respiratory signal and/or a respiratory signal indicative of a health issue or condition, the onset of an illness or disease, or the cessation of respiration.

Because the devices disclosed herein can be worn by the user at, for example, the wrist, they are less cumbersome for subjects to wear during sleep and do not interfere with or interrupt the subjects' sleep. It has been previously thought that accelerometers could only be used to monitor respiratory rates at locations on the body that exhibit large-scale motions resulting from breathing, i.e., the chest or stomach areas. Nonetheless, the present disclosure provides systems, devices and methods for determining respiratory rates from micro-motions not previously monitored by known devices. The micro-motions can be detected using one or more accelerometers configured as described herein, comparing one or more output signals of such accelerometer(s), magnifying and filtering such signals, and determining one or more qualities of the resulting signals including, but not limited to, waveform amplitude, wavelength, signal-to-noise ratio ("SNR"), or variance.

The monitoring devices may further comprise other components for monitoring the subject's heart rate (e.g., an optical sensor), tracking the user's physical location (e.g., a GPS module), a time keeping component (e.g., a clock, stopwatch, and/or timer), and one or more communication modules. The data from one or more such components may be used in conjunction with the collected respiration information to make further determinations and/or inferences regarding the subject's activity level, wellness, sleep state, or physiological state.

In embodiments where the monitoring device comprises an optical sensor for measuring a subject's heart rate, that information can be used to derive a respiration rate. However, continuous use of the optical sensor presents power management issues. A device operating an optical sensor continuously will consume considerably more power than a device that operates the optical sensor intermittently or only in situations in which optical detection has been triggered, is required, or would otherwise be desirable.

In one embodiment, monitoring devices described herein may utilize the one or more accelerometers to monitor a user's respiration rate (i.e., breaths/minute) by counting the number of breaths taken by a user in a predetermined time frame (e.g., 5 seconds, 30 seconds, 5 minutes, 30 minutes, etc.). This has the advantage of conserving the battery power consumption of the device as the accelerometer(s) requires significantly less power compared to the light sources of the optical sensor. In some examples, where a respiratory condition or event is detected using the accelerometer data, the optical signal can be activated to measure heart rate or respiratory rate. In this manner, the optical sensor can be used in a power-conserving way to confirm the data provided by the accelerometer(s).

Additional objects and advantages of the present disclosure will be set forth in part in the description which follows, and in part will be obvious from the description, or may be learned by practice of the disclosure.

It is to be understood that both the foregoing general description and the following detailed description are illustrative and explanatory only.

The accompanying drawings, which are incorporated in and constitute a part of this specification, illustrate several embodiments and together with the description, serve to explain the principles of the disclosure.

DESCRIPTION OF THE EMBODIMENTS

Disclosed herein are embodiments of an apparatus for use in respiratory monitoring and analysis. Of course, these examples are only illustrative of the possibilities and the systems, devices, and methods described herein may be used in any suitable context.

In one aspect, an apparatus may comprise one or more accelerometers incorporated into a portable or wearable device. In other embodiments, rather than comprising one or more accelerometers, the portable or wearable device may communicate with another device or system comprising one or more accelerometers. In one embodiment, the device may comprise one or more three-axis accelerometers. In other embodiments, the device may comprise one or more single-axis accelerometers, two-axis accelerometers, or some other suitable accelerometers.

In another aspect, the apparatus may receive acceleration data from the one or more accelerometers and, based at least in part on the acceleration data, determine whether a subject is sleeping or resting. Upon a determination that the subject is sleeping, the received acceleration data can be used to extrapolate respiration information. In further embodiments, the apparatus may comprise (or be in communication with) a time keeping component. In such embodiments, the apparatus may further determine and/or record the duration of a subject's sleep and the subject's respiration rate (i.e., a number of breaths per time interval) during sleep.

In a further aspect, the apparatus may comprise or be in communication with a database containing one or more records associating detected respiration rates (or ranges of respiration rates) with respiration rates typically found during one or more sleep stages. The records may be unique to the subject or may be based on a larger sample size comprising a plurality of subjects. In one embodiment, a first range of respiration rates can be associated with "light sleep." A second range of respiration rates can be associated with "deep sleep." And a third range of respiration rates can be associated with "REM sleep."

Detected respiration rates and respiration signals can also be analyzed to detect the presence of a sleep event, such as sleep apnea or respiratory arrest. In one embodiment, a sleep event can be detected by a respiration rate that accelerates or decelerates beyond a threshold. In some embodiments, a sleep event can be detected by a respiration signal that increases or decreases in amplitude, wavelength, or some other characteristic beyond a threshold.

While the systems and devices described herein may be depicted as wrist worn devices, one skilled in the art will appreciate that the systems, devices, and methods described below can be implemented in other contexts, including the sensing, measuring, and recording of respiration data gathered from a device worn at any suitable portion of a user's body, including but not limited to, other portions of the arm, other extremities, and/or the head.

Reference will now be made in detail to certain illustrative embodiments, examples of which are illustrated in the accompanying drawings. Wherever possible, the same reference numbers will be used throughout the drawings to refer to the same or like items.

Figure 1:
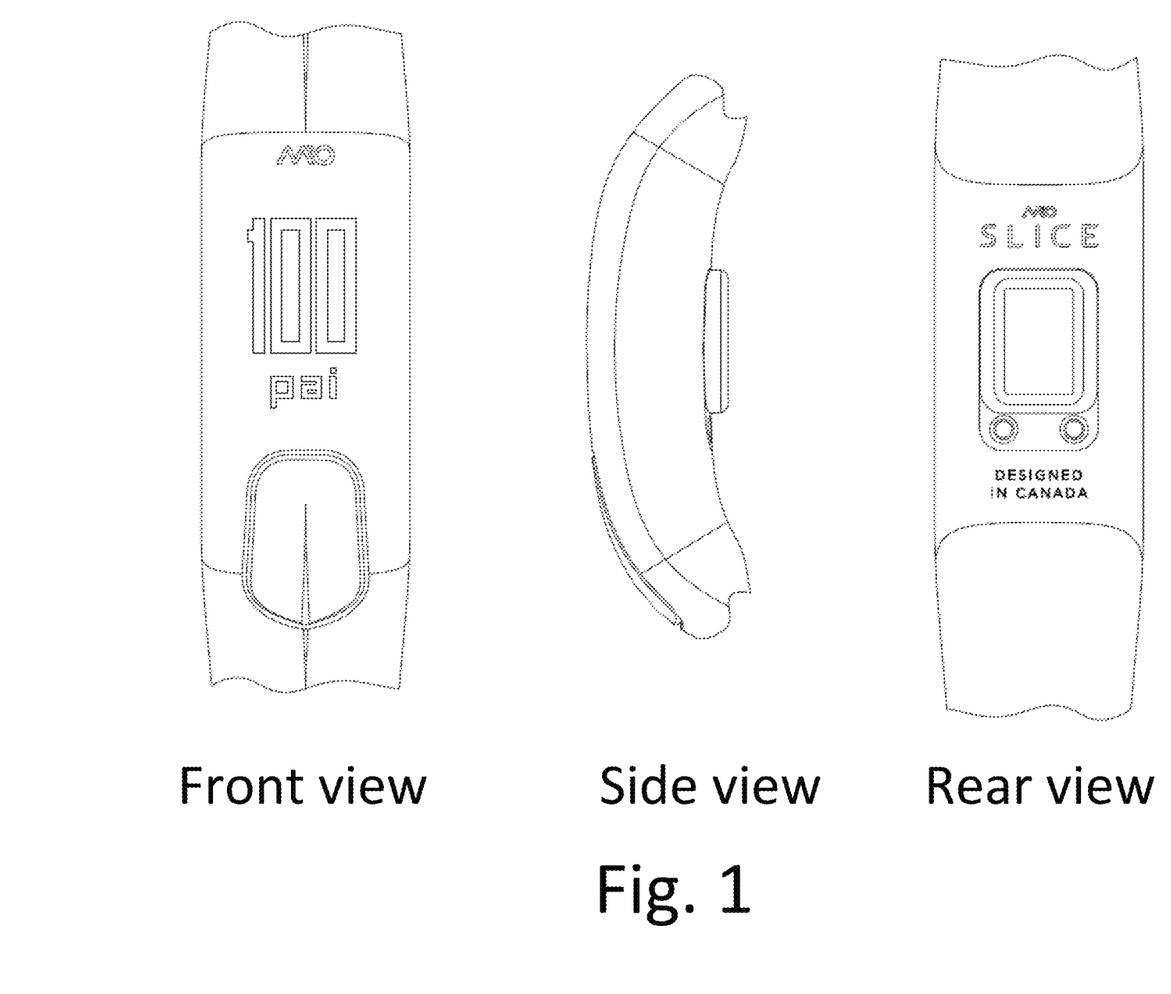
FIG. 1 provides an illustration of an example apparatus for performing respiratory analysis.

FIG. 1 depicts an illustrative embodiment of an apparatus 100. In one aspect, apparatus 100 may be a device worn by a user to sense, collect, monitor, and/or display information pertaining to the user's activity and/or one or more physiological parameters. In the depicted embodiment, apparatus 100 may comprise a wrist band. In alternative embodiments, apparatus 100 may be a bracelet, watch, or an arm band. In further embodiments, apparatus 100 may be any wearable monitor device configured for positioning at a user's wrist, arm, another extremity of the user, or some other suitable area of the user's body.

In another aspect, apparatus 100 may comprise one or more accelerometers (not depicted) and components for processing and displaying information that may or may not be related to a user's past or present activity, activity level, physical training sessions, or general wellness and/or one or more physiological parameters of a user. For example, in one embodiment, apparatus 100 may sense, process, and/or display the time, a timer or stopwatch, a distance traveled, a pace, a speed, calories burned, steps taken, step rate, an activity level, heart rate information, and/or other user- or activity-specific information. In a further aspect, apparatus 100 may house a display unit 110 for displaying or otherwise conveying information to the user. In one embodiment, display unit 110 may comprise a dot matrix liquid crystal display. In alternative embodiments, display unit 110 may comprise some other suitable display.

In a further aspect, apparatus 100 may comprise a casing 120 and one or more bands 130 extending from opposite edges of casing 120 for securing apparatus 100 to the user. In one embodiment, band(s) 130 may comprise an elastomeric material. In alternative embodiments, band(s) 130 may comprise some other suitable material, including but not limited to, a fabric or metal material.

Apparatus 100 may further comprise one or more buttons or switches 140 operable for accepting input from the user. Buttons 140 may comprise any suitable device for accepting input from the user including, but not limited to, a button, switch, touchscreen, or sensor. FIG. 1 depicts a single button 140, positioned adjacent display unit 110. Other embodiments, however, may comprise fewer or additional buttons. Moreover, the buttons may be located at any suitable location on apparatus 100.

In further embodiments, buttons 140 may be incorporated into display unit 110. For example, buttons 140 may comprise "soft" buttons configured to accept input from the user via a touchscreen.

In another aspect, the user may manipulate buttons 140 for setting the time display, establishing the operational mode of the heart rate monitor, reviewing respiration information, and/or otherwise configuring/interacting with apparatus 100 during use.

Display unit 110 may be configured to display information to the subject in the form of text, lights, and/or icon(s). For example, display 110 can be configured to display sleep information or respiration information during monitoring. Display 110 can also be used to indicate battery conditions, the time of day, the mode in which apparatus 100 is operating (such as "sleep" or "active" mode), the subject's heart rate, or the subject's respiration rate. Of course, the aforementioned examples are only illustrative of the possibilities. Fewer, additional, or alternative text, information, and/or icon(s) for display are also possible.

It should be noted that although a wrist band-like embodiment of apparatus 100 is depicted in FIG. 1, apparatus 100 may comprise alternative wearable embodiments such as watches, bracelets, straps, or clips. Such embodiments may include some or all of the features of the watch embodiment described above. For example, some embodiments may not comprise a display unit 110 or a casing 120. Rather, the various components of apparatus 100 may be housed or embedded in a single strap 130. In such embodiments, information may be conveyed to a user using tactile feedback (e.g., vibration), sound (e.g., tones of varying volume, pitch, frequency, and duration), and light (e.g., LEDs of one or more colors that may blink or be illuminated for some predetermined period).

In another aspect, apparatus 100 may be configured to communicate information to a subject via a secondary device such as a smart phone, tablet, or personal computer. In such embodiments, information collected, analyzed, or stored at apparatus 100 may be communicated to a secondary device for further analysis, storage, or presentation to the user. Conversely, apparatus 100 may be configured to receive information from such secondary devices for further analysis, storage, or presentation to the user.

Figure 2:
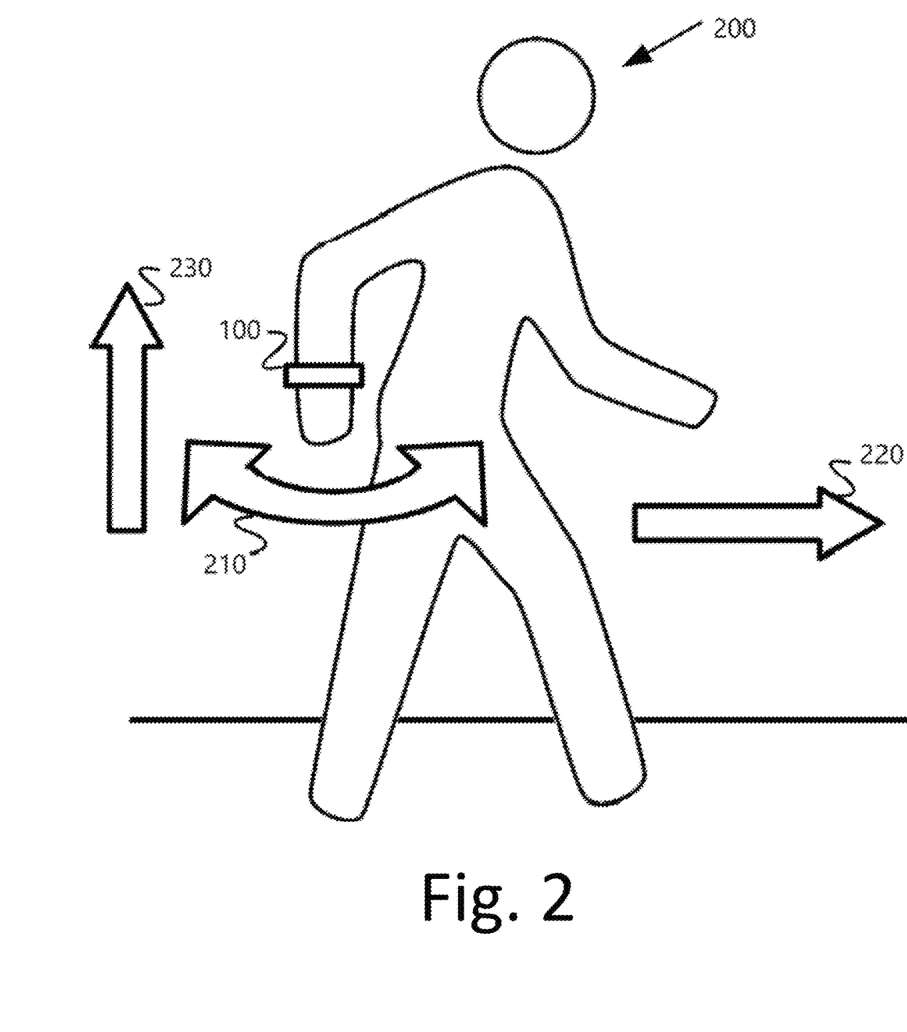
FIG. 2 provides an illustration of an example apparatus for performing respiratory analysis in use by a user.

FIG. 2 depicts an illustrative embodiment of apparatus 100 in use. In one aspect, subject 200 may wear apparatus 100 during an activity. In the embodiment depicted in FIG. 2, apparatus 100 is a wrist-worn device.

In one aspect, apparatus 100 may comprise one or more accelerometers (not depicted), including but not limited to, one or more three-axis accelerometers. Generally, one or more accelerometers may be configured to convert the movement or acceleration of a body into digital measurements. The acceleration data collected or transmitted by the accelerometer(s) may comprise information regarding the frequency, duration, intensity, and patterns of movement associated with the body, all or some of which may be used to determine when a user has taken a step and/or an activity type that the user may be engaged in. For example, in some embodiments, patterns associated with a user walking or running may be identified and movements exceeding predetermined amplitude thresholds may be counted as a step. A frequency associated with such threshold-exceeding amplitudes may be used, for example, to determine whether the user is walking or running. In further embodiments, moving averages of such data may be used to further refine a step count and/or take potential uneven steps or missteps into account. In other embodiments, other systems, devices, or methods may be used to determine when a user takes a step and/or determine other activity information.

As shown in FIG. 2, the accelerometer(s) may collect acceleration data attributable to the swinging or rhythmic movement 210 specific to a body portion or appendage associated with apparatus 100 (e.g., the swinging motion of an arm during running or walking), the user's forward or backward movement 220 resulting from a step, and/or the user's upward or downward movement 230 resulting from or following a step, respectively.

In use, acceleration data attributable to swinging/rhythmic movement 210 that masks or interferes with acceleration data attributable to movements 220 and 230 may be accounted for so as to arrive at accurate step determinations or other activity information. Further details regarding the interpretation of acceleration data for determining when a user takes a step and/or for the assessment of activity information are beyond the scope of this disclosure as several such systems, devices, and methods are known.

Figure 3:
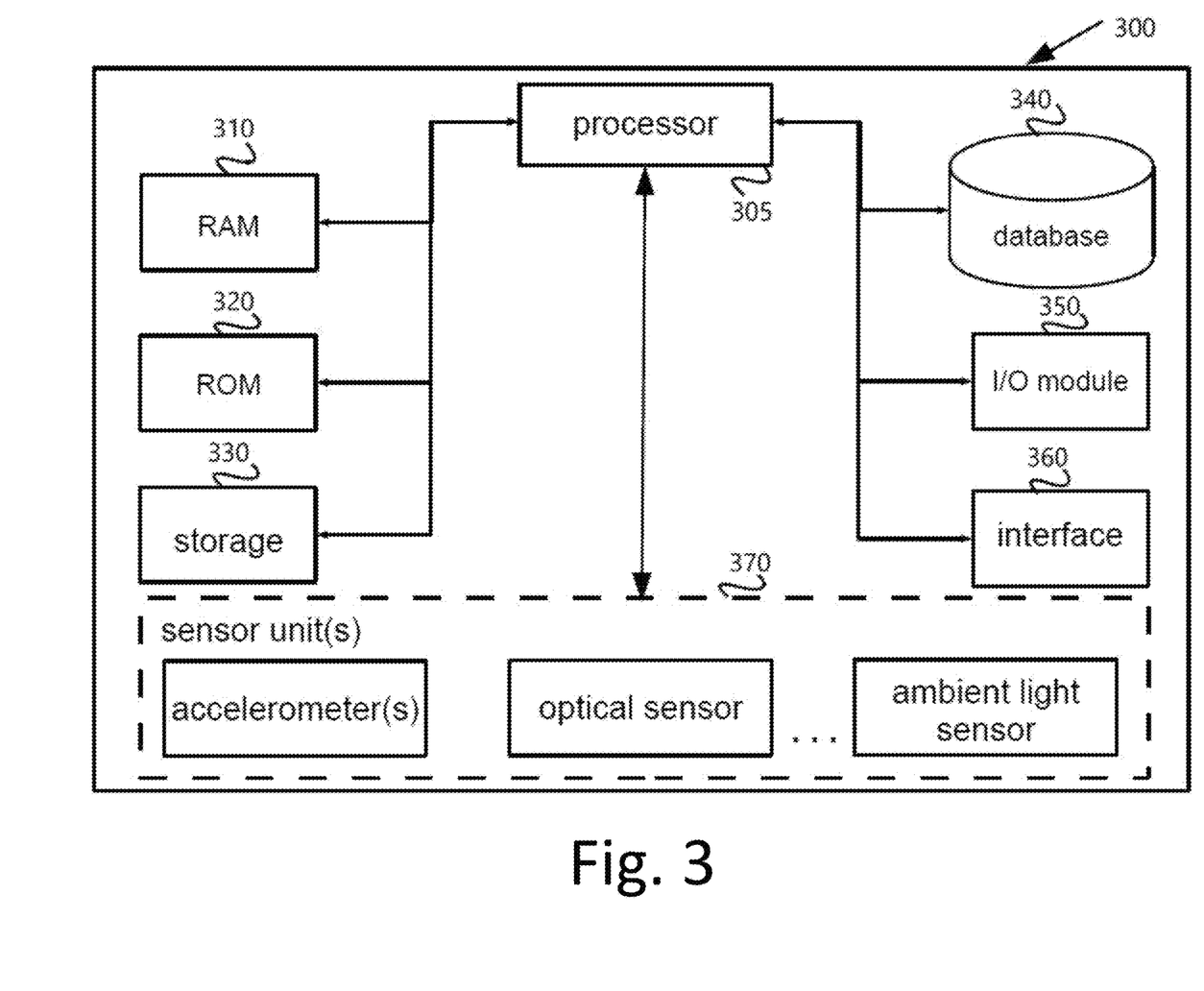
FIG. 3 provides a diagram of an example processor-based computing system that can be used for performing respiratory analysis.

FIG. 3 depicts an illustrative processor-based computing system 300 representative of the type of computing system that may be present in or used in conjunction with any aspect of apparatus 100 comprising electronic circuitry. For example, processor-based computing system 300 may be used in conjunction with any one or more of transmitting signals to and from the one or more accelerometers, sensing or detecting signals received by one or more sensors of apparatus 100, processing received signals from one or more components or modules of apparatus 100 or a secondary device, and storing, transmitting, or displaying information. Computing system 300 is illustrative only and does not exclude the possibility of another processor- or controller-based system being used in or with any of the aforementioned aspects of apparatus 100.

In one aspect, system 300 may include one or more hardware and/or software components configured to execute software programs, such as software for storing, processing, and analyzing data. For example, system 300 may include one or more hardware components such as, for example, processor 305, a random-access memory (RAM) module 310, a read-only memory (ROM) module 320, a storage system 330, a database 340, one or more input/output (I/O) modules 350, an interface module 360, and one or more sensor modules 370. Alternatively and/or additionally, system 300 may include one or more software components such as, for example, a computer-readable medium including computer-executable instructions for performing methods consistent with certain disclosed embodiments. It is contemplated that one or more of the hardware components listed above may be implemented using software. For example, storage 330 may include a software partition associated with one or more other hardware components of system 300. System 300 may include additional, fewer, and/or different components than those listed above. It is understood that the components listed above are illustrative only and not intended to be limiting or exclude suitable alternatives or additional components.

Processor 305 may include one or more processors, each configured to execute instructions and process data to perform one or more functions associated with system 300. The term "processor," as generally used herein, refers to any logic processing unit, such as one or more central processing units (CPUs), digital signal processors (DSPs), application specific integrated circuits (ASICs), field programmable gate arrays (FPGAs), and similar devices. As illustrated in FIG. 3, processor 305 may be communicatively coupled to RAM 310, ROM 320, storage 330, database 340, I/O module 350, interface module 360, and one more sensor modules 370. Processor 305 may be configured to execute sequences of computer program instructions to perform various processes, which will be described in detail below. The computer program instructions may be loaded into RAM for execution by processor 305.

RAM 310 and ROM 320 may each include one or more devices for storing information associated with an operation of system 300 and/or processor 305. For example, ROM 320 may include a memory device configured to access and store information associated with system 300, including information for identifying, initializing, and monitoring the operation of one or more components and subsystems of system 300. RAM 310 may include a memory device for storing data associated with one or more operations of processor 305. For example, ROM 320 may load instructions into RAM 310 for execution by processor 305.

Storage 330 may include any type of storage device configured to store information that processor 305 may need to perform processes consistent with the disclosed embodiments.

Database 340 may include one or more software and/or hardware components that cooperate to store, organize, sort, filter, and/or arrange data used by system 300 and/or processor 305. For example, database 340 may include user profile information, historical activity and user-specific information, physiological parameter information, predetermined menu/display options, and other user preferences. Alternatively, database 340 may store additional and/or different information.

I/O module 350 may include one or more components configured to communicate information with a user associated with system 300. For example, I/O module 350 may comprise one or more buttons, switches, or touchscreens to allow a user to input parameters associated with system 300. I/O module 350 may also include a display including a graphical user interface (GUI) and/or one or more light sources for outputting information to the user. I/O module 350 may also include one or more communication channels for connecting system 300 to one or more secondary or peripheral devices such as, for example, a desktop computer, a laptop, a tablet, a smart phone, a flash drive, or a printer, to allow a user to input data to or output data from system 300.

Interface 360 may include one or more components configured to transmit and receive data via a communication network, such as the Internet, a local area network, a workstation peer-to-peer network, a direct link network, a wireless network, or any other suitable communication channel. For example, interface 360 may include one or more modulators, demodulators, multiplexers, demultiplexers, network communication devices, wireless devices, antennas, modems, and any other type of device configured to enable data communication via a communication network.

System 300 may further comprise one or more sensor modules 370. In one embodiment, sensor modules 370 may comprise one or more of an accelerometer module, an optical sensor module, and/or an ambient light sensor module. Of course, these sensors are only illustrative of a few possibilities and sensor modules 370 may comprise alternative or additional sensor modules suitable for use in apparatus 100. It should be noted that although one or more sensor modules are described collectively as sensor modules 370, any one or more sensors or sensor modules within apparatus 100 may operate independently of any one or more other sensors or sensor modules. Moreover, in addition to collecting, transmitting, and receiving signals or information to and from sensor modules 370 at processor 305, any one or more sensors of sensor module 370 may be configured to collect, transmit, or receive signals or information to and from other components or modules of system 300, including but not limited to database 340, I/O module 350, or interface 360.

As described above, the one or more accelerometers of apparatus 100 can be used to detect large-scale motions of a subject indicative of physical activity (e.g., steps, running, walking, swimming, etc.). The same accelerometers can be used to determine the onset of a rest or sleep period through the detection of a lack of motion. However, the sensitivity of the accelerometer(s) that detect large-scale motions aren't sensitive enough to detect movement at the wrist (or other suitable location of the body) due to breathing. In one embodiment, upon determining that the subject is engaged in rest or sleep, the sensitivity of the accelerometer(s) can be reconfigured to detect significantly smaller motions ("micro-motions"). Alternatively, apparatus 100 may comprise one or more accelerometers that are dedicated to, and configured for, detecting micro-motions while one or more other accelerometers are used to detect large-scale motions.

To detect micro-motions, an accelerometer can be configured to increase its sensitivity and sampling rate. The sensitivity of an accelerometer is expressed in terms of millivolts per G-force (mV/g). Where an accelerometer configured for large-scale motions may use 7-12 g as the denominator, an accelerometer configured for micro-motion detection may use 0.001-5.0 g. In some embodiments, an accelerometer for micro-motion detection may use 1-4 g.

Additionally, it may be advantageous to increase the sampling rate of an accelerometer for measuring micro-motions as compared to when measuring large-scale motions. For example, where a frequency of 1-3 Hz may be sufficient to sample large-scale motions, a frequency of 5 Hz-1 KHz may be desirable when detecting micro-motions. In some embodiments, a frequency of 5-100 Hz may be desirable. Again, regardless of the disparate sensitivity and/or sampling frequency between accelerometer settings for measuring large-scale and micro-motions, the same accelerometer(s) in apparatus 100 can either be reconfigured upon detection of a rest or sleep state, or alterative accelerometer(s) having a higher sensitivity can be activated during the rest or sleep state. If an accelerometer that is calibrated for large-scale motions is used to measure micro-motions, the amplitude of the output signal will not be great enough for accurate analysis. Conversely, if an accelerometer calibrated for micro-motions is used to measure large-scale motions, the amplitude of the output signal will always be very large, resulting in a saturated signal that provides little useful information.

Figure 4A:
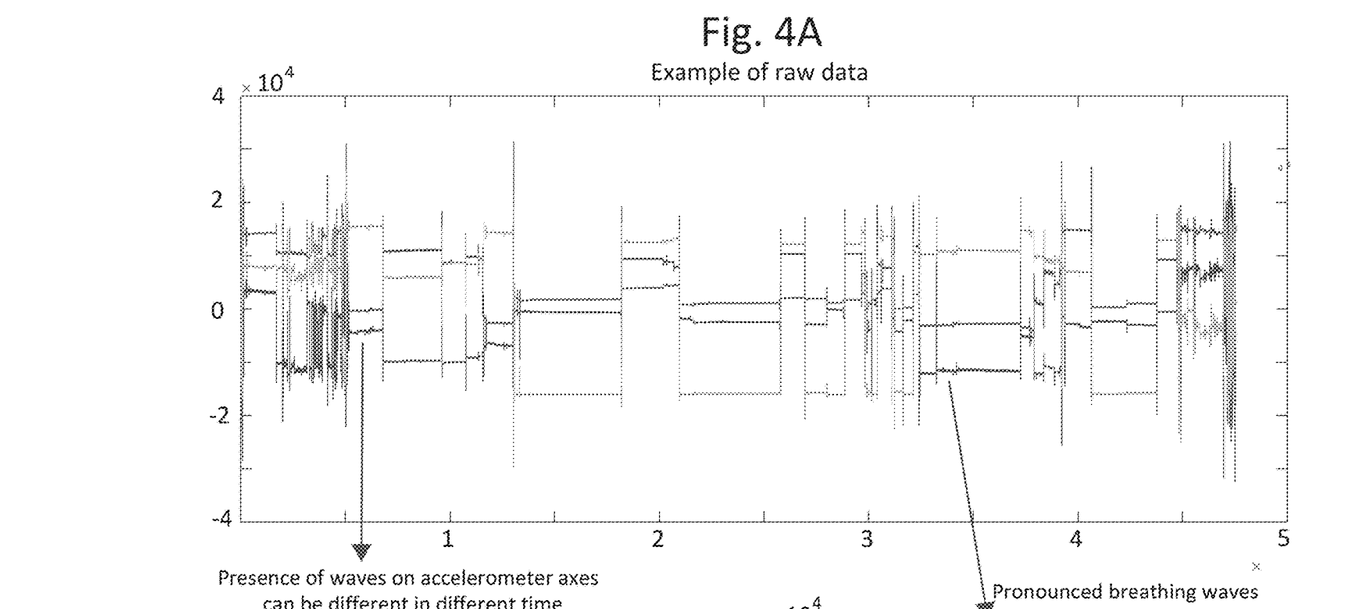
FIG. 4A provides a graphical representation of example raw data collected by a three-axis accelerometer calibrated to detect micro-motion during a rest or sleep state.
Figure 4B:
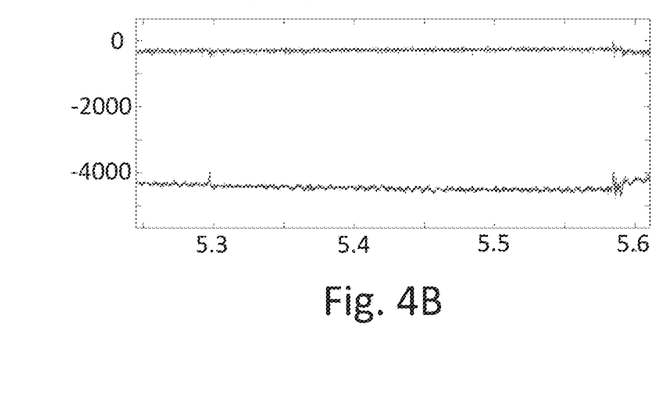
FIG. 4B provides a zoomed-in view of a portion of the example raw data of FIG. 4A.

FIG. 4A depicts an example of the raw data collected by a three-axis accelerometer calibrated to detect micro-motion during a rest or sleep state. In this embodiment, apparatus 100 comprising the accelerometer is located in a wearable band worn at the wrist of the subject. Based on the output signals, one can discern when large-scale movements (such as the subject shifting his weight, rolling over, or moving an arm) have taken place by the spikes in the accelerometer output. When such spikes occur, they can mask the micro-motions caused by respiration. However, where the output signals are stable, one can magnify and smooth the output signal to discern a respiratory signal. Moreover, where a three-axis (or two-axis) accelerometer is used, one axis may provide a more stable output signal than another axis. This disparity in the outputs of two axis of three-axis accelerometer is depicted in FIG. 4B.

Figure 4C:
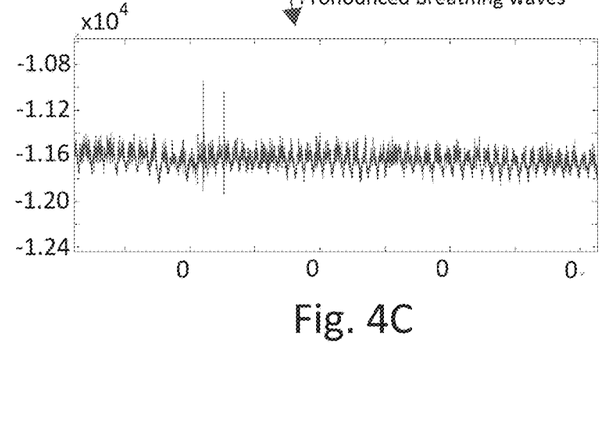
FIG. 4C provides a zoomed-in view of a portion of the example raw data of FIG. 4A.

At any given time during the rest or sleep state, the output of each axis of the accelerometer can be assessed and the clearest signal (relatively higher amplitudes, relatively stable frequencies) can be selected for respiratory analysis. A magnified view of a signal output from one of the accelerometer axis is depicted in FIG. 4C.

Figure 5:
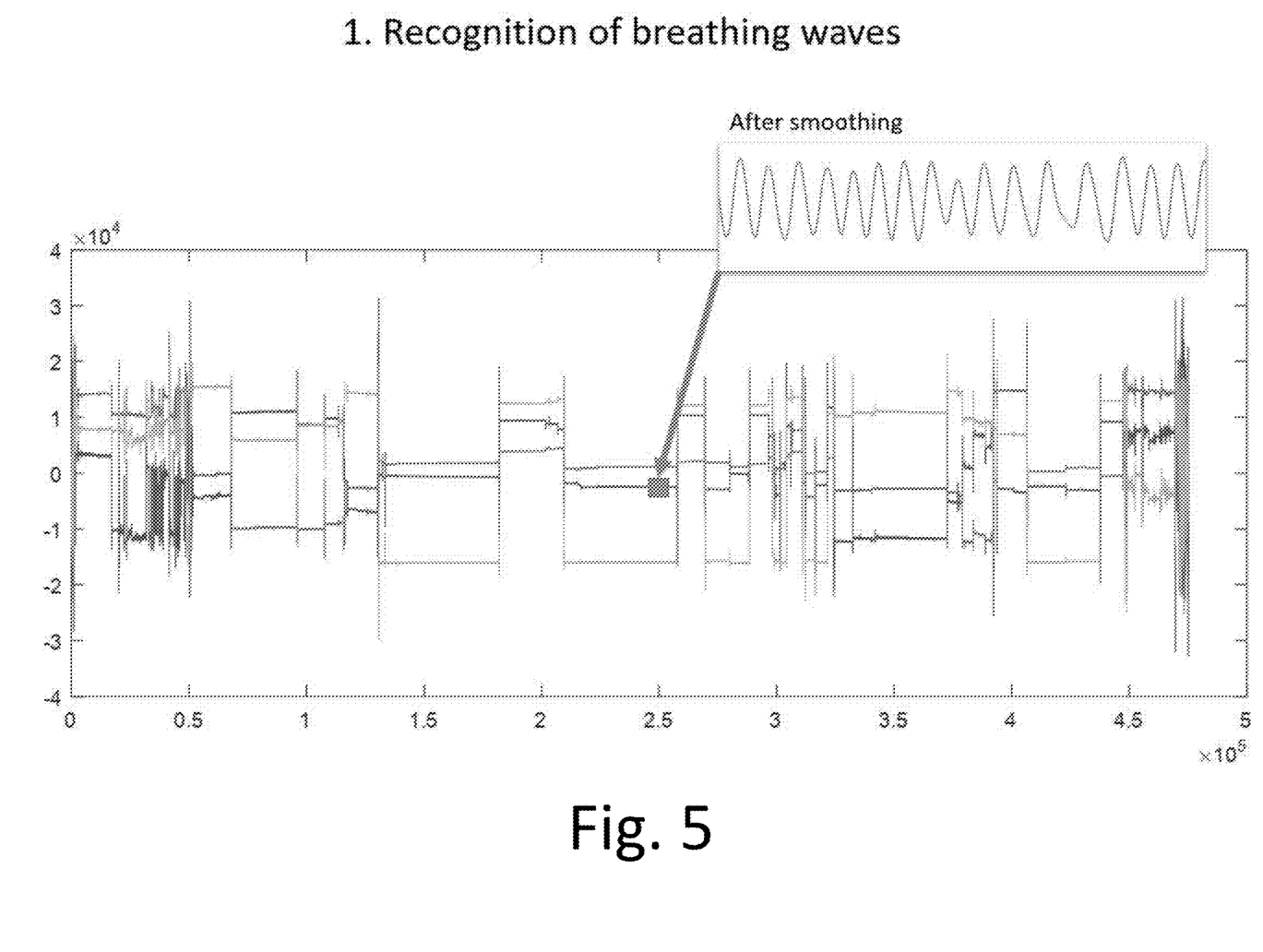
FIG. 5 provides an example of smoothing raw data collected by an accelerometer.

FIG. 5 depicts what such a single-axis output looks like after it has been magnified and smoothed using a smoothing filter (several of which are known) and noise has been removed (several methods of which are known). The smoothing and/or noise filters can be implemented using either hardware or software components. One can see where a period of no large-scale motions was selected, then the clearest axis output was selected, then the selected output was magnified and smoothed resulting in a series of waves of similar amplitude and frequency.

Figure 6:
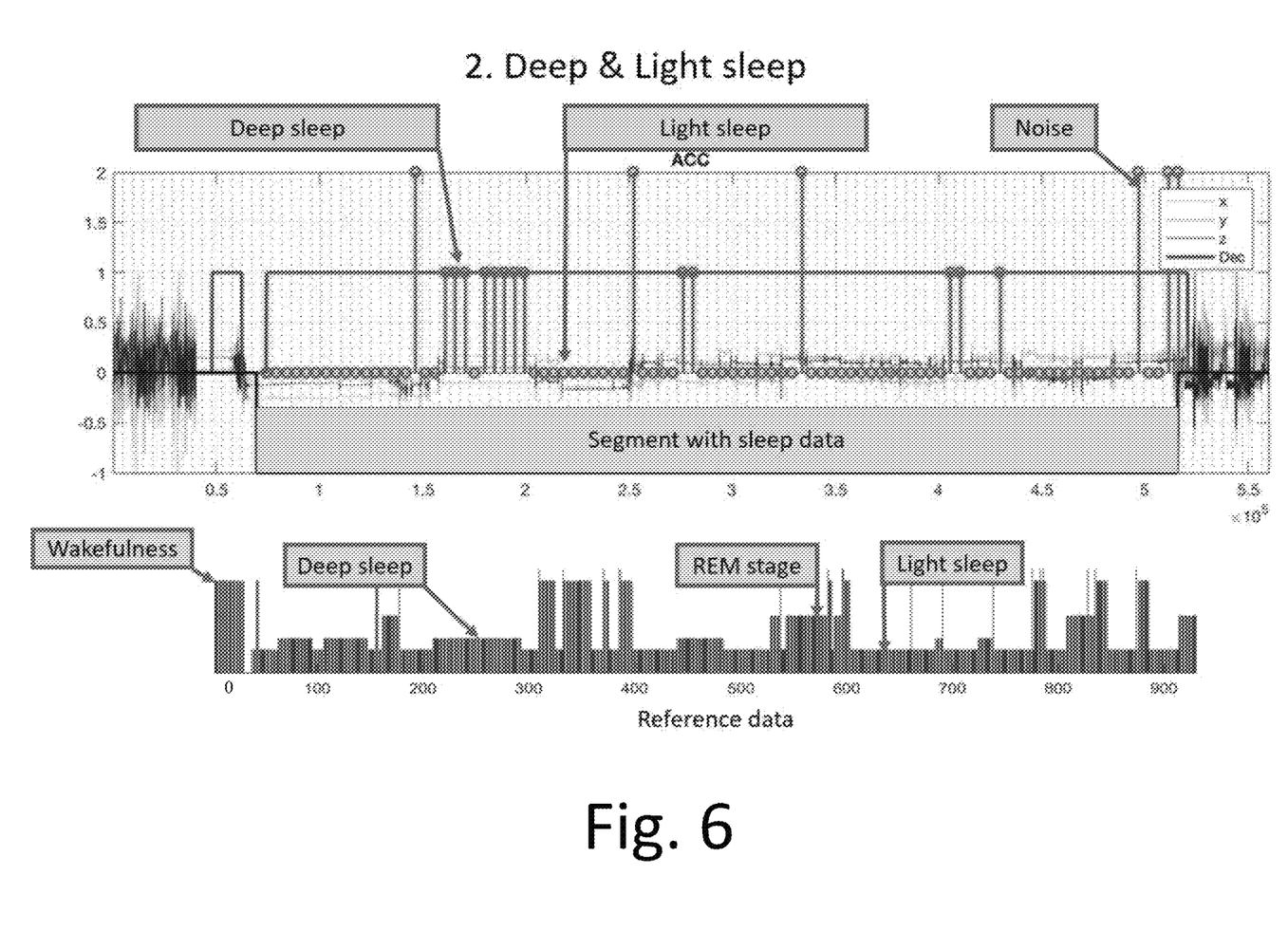
FIG. 6 provides an example illustration of using accelerometer output to identify sleep stages.

FIG. 6 depicts how the output of the accelerometer(s) can be used not only to detect sleep but to identify sleep stages (i.e., light sleep, deep sleep, and REM sleep). During a sleep stage, breathing can become heavier or lighter resulting in larger or smaller amplitude, respectively, output signals from the accelerometer(s). Noise within an output signal can also be used to determine sleep stage, particularly when viewed in light of signal amplitude. Thus, amplitude, noise, the signal-to-noise ratio ("SNR"), or the signal variance of the output signals can be indicative of sleep stage. Generally, deep breathing (relatively large amplitude signals) can be associated with deep stage sleep. In other embodiments, a relatively high SNR (e.g., 1:1) can be indicative of deep stage sleep. In alternative embodiments, relatively low signal variance can be used to determine deep stage sleep. Relatively light or shallow breathing (relatively small amplitude signals) can be associated with light stage sleep. In other embodiments, a relatively low SNR (e.g., approximately 0) can be indicative of light stage sleep. In alternative embodiments, relatively high signal variance can be used to determine light stage sleep. Similar to light stage sleep, REM stage sleep can be associated with shallow breathing (relatively small amplitude signals). In particular, relatively shallow breathing (small amplitude signals) against a background of high variance (variation in the output waveform) can be associated with REM stage sleep.

Figure 7:
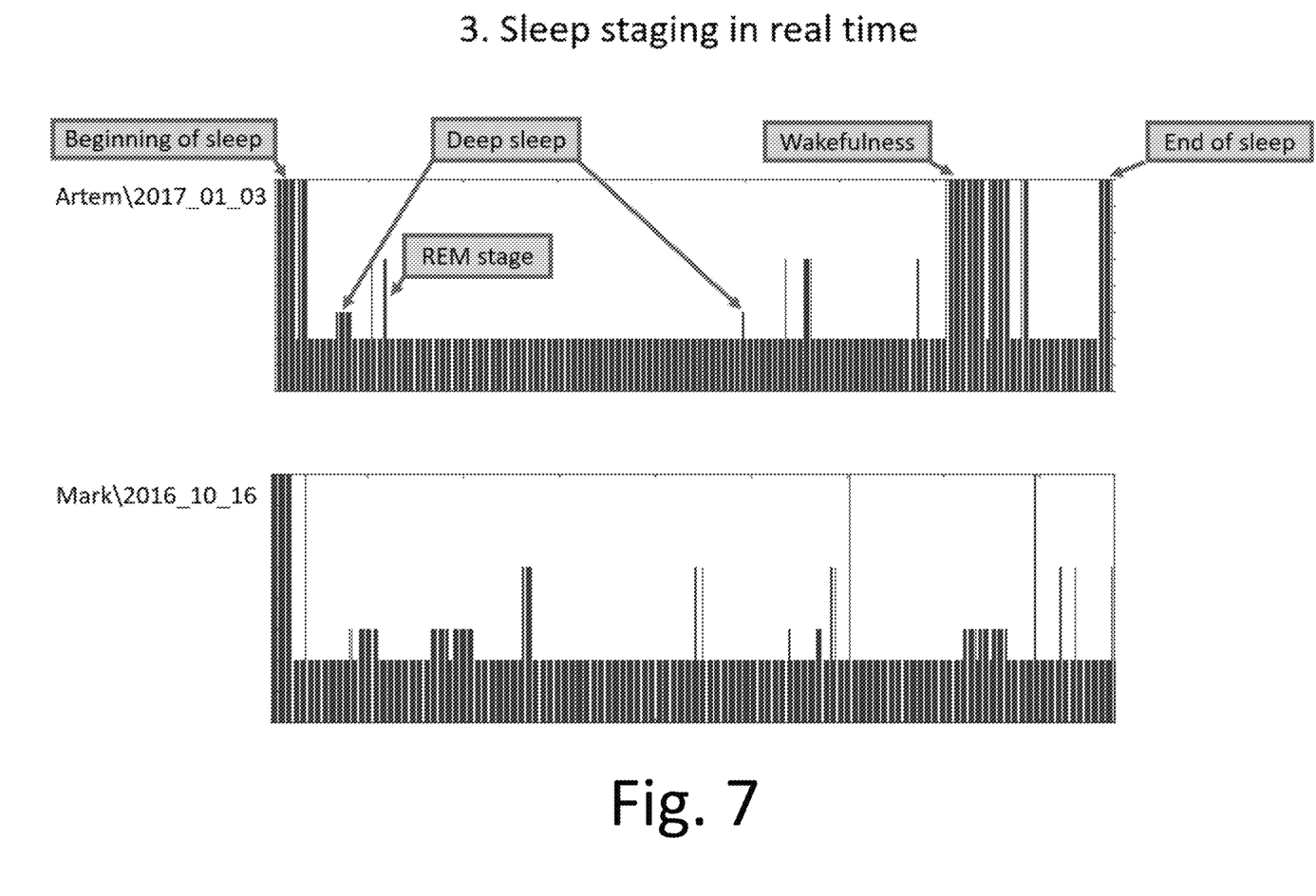
FIG. 7 provides an example output signal for two sleep subjects.

FIG. 7 depicts the sleep stages of two subjects. The output signal from an axis of the accelerometer(s) can be used to determine when sleep commenced, as well as instances of light stage, deep stage, and REM stage sleep. Additionally, when the output signal becomes saturated, it can be determined that the subject was either restless or awake.

With the data collected from the accelerometer(s) described above, a number of insights can be gained into a subject's sleeping habits. For example, the total duration of physiological sleep can be determined, a ratio of deep to light sleep (or REM to other sleep) can be determined, the number of instances the subject awoke during a sleep state can be determined, or the time of the first REM-stage sleep can be determined (which may have implications in a sports/recovery application).

Other components of apparatus 100 can also be configured to aid in a subject's sleep, falling asleep, or waking up. For example, studies have shown that particular respiratory rates (e.g., 6 breaths per minute) can activate a subject's parasympathetic branch of ANS and make it easier for a subject to fall asleep. Apparatus 100 can use respiratory data in conjunction with tactile feedback (e.g., vibrations), audible sounds, or visual indicators (e.g., flashing lights) to pace the subject's breathing. In other words, apparatus 100 may vibrate, beep, or light up when the subject should inhale and/or exhale. In further embodiments, the intensity or the vibration, volume of the beep, or intensity of the light could be used to inform the subject as to the depth of the breaths they should be, or are, taking. By specifying the respiratory rate and depth of the subject's breathing, apparatus 100 can guide the subject to sleep.

Apparatus 100 can also be used to gently wake a subject. Waking from a deep sleep can be disruptive and disorienting to a subject. Because apparatus can recognize when the subject is in a light stage sleep, it can wake the subject at an advantageous time.

In one embodiment, a subject may input a window of time during which he would like to be woken (e.g., 6:00 am-7:00 am). When the subject is awake or is in a light stage sleep during this timeframe, apparatus 100 can initiate a wake-up routine. Using the communication module of apparatus 100 in a "smart home" environment, apparatus can transmit a signal to turn a light or gradually increase the brightness of lights proximate the subject. Should the end of the timeframe be reached, and the subject has neither awoken nor entered light stage sleep, apparatus 100 can initiate the wake-up routine to wake the subject.

While in this example, a smart home light source is used to wake the subject, it should be recognized that any other suitable device can be used. For example, apparatus 100 can begin to vibrate, beep, or light up. Alternatively or additionally, apparatus 100 can communicate with other smart home devices, such as blinds, A/V equipment, appliances, etc.

Figure 8:
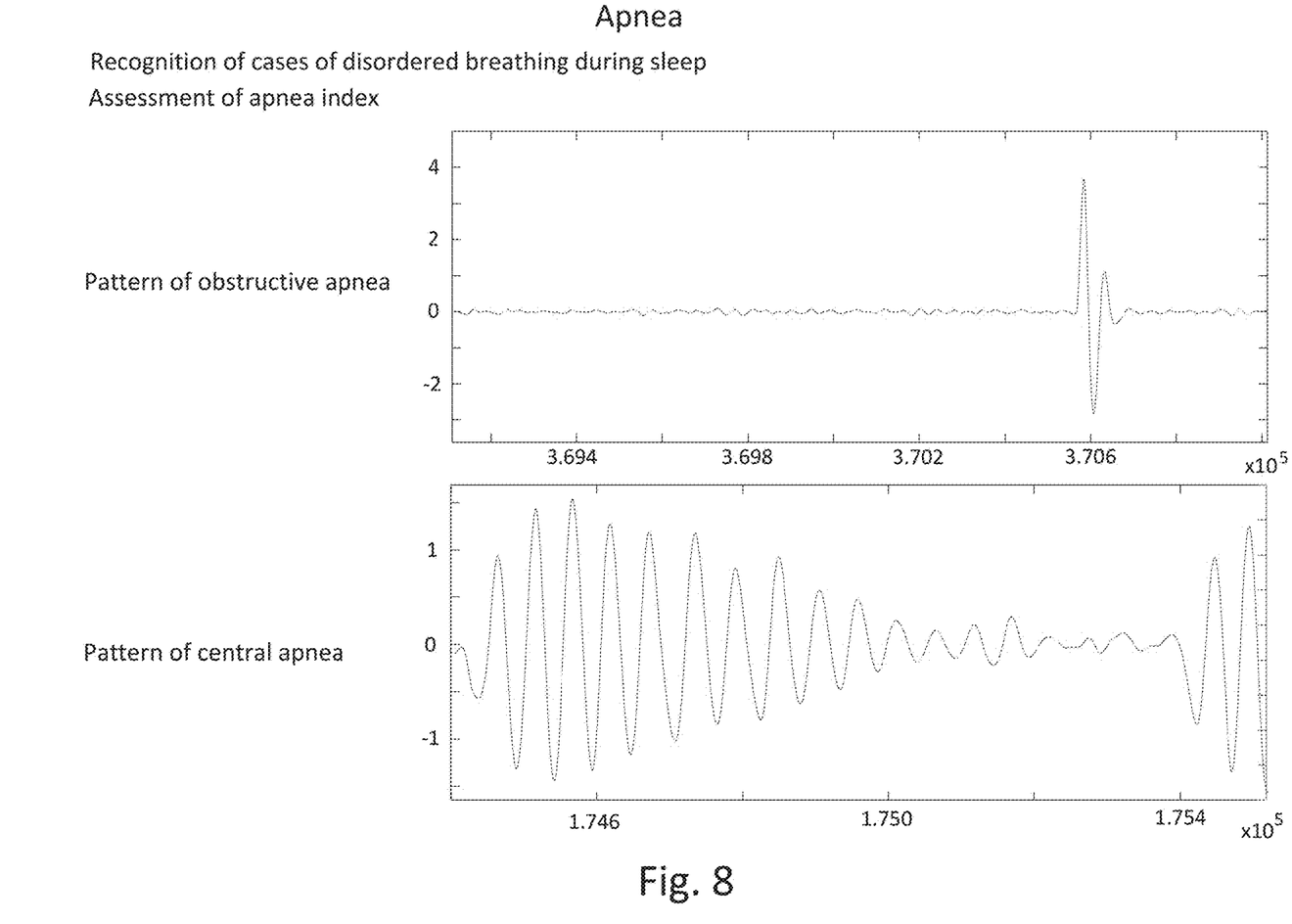
FIG. 8 provides examples of respiratory signals indicative of sleep apnea events.

Apparatus 100 can also be configured to detect sleep events, such as sleep apnea or respiratory arrest. FIG. 8 provides examples of respiratory signals indicative of sleep apnea events. In the top graph, a brief episode of extremely deep breathing is depicted. This can result when the subject has been breathing shallowly for an extended period of time and needs more oxygen. The bottom graph of FIG. 8 depicts another type of sleep apnea. In this situation, regular breathing tapers off and becomes very shallow until the subject needs oxygen and starts breathing normally again.

Neither of these patterns, in isolation, is indicative of sleep apnea or any other disorder. However, if numerous instances of such patterns are exhibited during a sleep state, it can be diagnosed as sleep apnea. For example, one or two instances where the accelerometer(s) of apparatus 100 output signals similar to those shown in FIG. 8 over the course of several hours would not necessarily lead to a sleep apnea diagnosis. But if the same signal patterns are experienced a number of times in a given time period (e.g. 10 times in 6 hours) over some threshold, or if one of the signal patterns is seen once every time period (e.g., once an hour, once every half-hour) over some percentage of the overall sleep state (e.g., 5% or 10%), then a sleep apnea diagnosis can be made.

Similarly, apparatus 100 can monitor for instances of respiratory arrest (i.e., the cessation of breathing). This can be a sign of a significant problem or emergency. In one embodiment, the accelerometer(s) of apparatus 100 can determined that no respiration signals (i.e., micro-motions) are detected at the subject. This may cause the optical sensor to activate and check for respiration or a heartbeat. If a heartbeat is found or the optical detector determines that apparatus 100 is not being worn by the subject, then no further action may be taken or respiratory monitoring using the accelerometer(s) may continue. On the other hand, if no respiration or heartbeat is determined by the optical sensor, then the communication module of apparatus 100 can transmit an emergency signal or initiate an emergency communication. For example, apparatus 100 can instruct a BLUETOOTH-paired smartphone to call 911. Or apparatus 100 can transmit a signal to a device belonging to a caregiver or medical professional. In some embodiments, the period of non-responsiveness (i.e., no respiration or no heartbeat) must last some minimum duration of time (e.g., one minute) before any emergency or alert communications are initiated.

Apparatus 100 can also be used to aid a subject in taking a nap (i.e., a sleep state of relatively short duration, e.g., 30 minutes, 1 hour). If one enters deep stage sleep during a nap, he or she may feel very drowsy or groggy when they wake up and may be unable to perform at an optimal level for some amount of time. In one embodiment, the subject can initiate a napping state at apparatus 100. Apparatus 100 can monitor the respiratory rate of the subject during the nap and wake the subject (as described above with respect to other embodiments) when apparatus 100 determines the onset of deep stage sleep (as described above with respect to other embodiments). In this manner, the subject will be in an alert state upon waking and will not feel the drowsiness associated with being woken out of deep stage sleep.

While illustrative embodiments have been illustrated and described, it will be appreciated that various changes can be made therein without departing from the spirit and scope of the disclosure. Moreover, the various features of the embodiments described herein are not mutually exclusive. Rather any feature of any embodiment described herein may be incorporated into any other suitable embodiment.

Additional features may also be incorporated into the described systems, devices, and methods to improve their functionality. For example, those skilled in the art will recognize that the disclosure can be practiced with a variety of activity monitoring devices, including but not limited to activity, wellness, heart rate, blood pressure, exertion, and perspiration monitors, and that various components, sensors, and modules may be employed within such monitoring devices. The devices may or may not comprise one or more features to ensure they are water resistant or waterproof. Some embodiments of the devices may be hermetically sealed or even surgically implanted in the user's body. Alternatively, some embodiments of the devices may be embedded or integrated with clothing items such as shirts, shorts, pants, jackets, or shoes, to name only a few examples.

Other embodiments of the aforementioned systems, devices, and methods will be apparent to those skilled in the art from consideration of the specification and practice of this disclosure. It is intended that the specification and the aforementioned examples and embodiments be considered as illustrative only.

What is claimed is:

1. A method for determining sleep characteristics based on movement data, comprising:
   providing a device that is configured to be worn as a wrist watch or bracelet, the device comprising a processor and an accelerometer configured to detect small motions of a user when the device is being worn by the user;
   calibrating the accelerometer to detect micro-motion during a rest or sleep state;
   detecting respiration with the micro-motions detected by the accelerometer, wherein detecting respiration with the accelerometer comprises:
   monitoring a respiration rate; and
   detecting an amplitude of an output signal provided by the accelerometer;
   storing the output signal from the accelerometer during sleep;
   applying a filter to a portion of the output signal, and
   determining, based at least in part on the filtered portion of the output signal, whether the user was sleeping during a time corresponding to the filtered portion of the output signal;
   wherein based on a determination that the user was sleeping, determining a sleep characteristic for at least a portion of the time corresponding to the filtered portion of the output signal of the accelerometer;
   wherein determining a sleep characteristic comprises determining whether the user was experiencing deep sleep, light sleep, or random-eve-movement ("REM") sleep, and determining that the user experienced a pattern of obstructive apnea or a pattern of central apnea.

2. The method of claim 1, wherein determining a sleep characteristic comprises comparing a portion of the filtered output signal to a stored pattern that is at least partially based on data collected from the user.

3. The method of claim 1, wherein the micro-motions of the user the accelerometer is configured to detect are based on setting the sensitivity of the accelerometer between 0.1-5.0 millivolts per G-force.

4. The method of claim 1, wherein the micro-motions of the user the accelerometer is configured to detect are based on setting a sampling rate of the accelerometer between 5-1000 Hz.

5. The method of claim 1, comprising a communication module and the communication module includes a step of transmitting a signal to turn on a light or gradually increase a brightness of lights proximate to a subject so that a wake-up routine is initiated or to wake up the subject.

6. The method of claim 1, further comprising magnifying the amplitude of the output signal and determining one or more qualities of a resulting magnified output signal, wherein the resulting magnified signal includes the amplitude in a graphical representation as a waveform amplitude, wavelength, signal-to-noise ratio, or variance.

7. The method of claim 1, wherein the filter is a smoothing filter where a selected output of the output signal is magnified and smoothed.

8. The method of claim 7, wherein the selected output when magnified provides a magnified output signal where large-scale movements are discernable from micro-motions.

9. The method of claim 1, further comprising:
   identifying patterns within the output signal of the accelerometer regarding respiration.

10. A device for determining sleep characteristics based on movement data, comprising:
    an accelerometer calibrated to detect micro-motions of a user during a rest or sleep state when the device is being worn by the user, wherein the micro-motions detected by the accelerometer comprise a respiration rate and an output signal with an amplitude;
    memory including non-transitory, computer-readable medium containing instructions for determining sleep characteristics from the micro-motions measured by the accelerometer;
    a processor configured to execute the instructions to perform stages comprising:
    storing the output signal from the accelerometer during sleep;

applying a filter to a portion of the output signal from the accelerometer;

determining, based at least in part on the filtered portion of the output signal, whether the user was sleeping during a time corresponding to the filtered portion of the output signal, the respiration rate of the user, and the amplitude of the output signal; and based on a determination that the user was sleeping, determining a sleep characteristic for at least a portion of the time corresponding to the filtered portion of the output signal;

determining a sleep characteristic comprises determining whether the user was experiencing deep sleep, light sleep, or random-eye-movement ("REM") sleep, and determining that the user experienced a pattern of obstructive apnea or a pattern of central apnea based upon the output signal of the accelerometer from the filter; and wherein the device is a wearable device that is configured to be positioned at the user's wrist.

11. The device of claim 10, wherein determining a sleep characteristic comprises comparing a portion of the filtered output signal to a stored pattern; and wherein the stored pattern is at least partially based on data collected from the user.

12. The device of claim 10, wherein the accelerometer is configured to detect micro-motions of a user based on setting the sensitivity of the accelerometer between 0.1-5.0 millivolts per G-force, and the accelerometer is configured to detect micro-motions of a user based on setting a sampling rate of the accelerometer between 5-1000 Hz.

13. The device of claim 10, wherein the device further includes an ambient light sensor module and an optical sensor and the ambient light sensor, the optical sensor, and the accelerometer operate independently of one another.

14. The device of claim 10, wherein the processor is configured to magnify the amplitude of the output signal so that a respiratory signal is discernable from a large-scale movement within the output signal.

15. The device of claim 10, further comprising a hardware component or a software component that implements the filter and magnifies and smooths a selected output of the output signal.

16. The device of claim 10, wherein the processor is configured to: identify patterns within the output signals of the accelerometer regarding the respiration.

17. A non-transitory, computer-readable medium containing instructions that, when executed by a processor of a computing device, causes the processor to perform stages for determining sleep characteristics based on movement data, the stages comprising:

calibrating an accelerometer to detect micro-motion during a rest or sleep state;

receiving data from the accelerometer regarding detected micro-motion of a user when the device is being worn by the user, wherein the micro-motions detected by the accelerometer comprise:

a respiration rate and an output signal with an amplitude;

receiving the output signal from the accelerometer configured to detect respiration;

storing the output signal from the accelerometer during sleep;

applying a filter to a portion of the output signal;

determining, based at least in part on the filtered portion of the output signal from the accelerometer, whether the user was sleeping during a time corresponding to the filtered portion of the output signal; and based on a determination that the user was sleeping, determining a sleep characteristic for at least a portion of the time corresponding to the filtered portion of the output signal;

determining a sleep characteristic comprises determining whether the user was experiencing deep sleep, light sleep, or random-eye-movement ("REM") sleep, and determining that the user experienced a pattern of obstructive apnea or a pattern of central apnea; and wherein the device being worn by the user is configured to be worn at the user's wrist.

18. The non-transitory, computer-readable medium of claim 17, wherein when the accelerometer detects no micro-motions, an optical sensor is activated to check for respiration or a heartbeat.

19. The non-transitory, computer-readable medium of claim 17, further comprising magnifying the output signal, wherein the processor, in applying the filter, smooths and filters a selected output.

20. The non-transitory, computer-readable medium of claim 17, further comprising:

identifying patterns within the output signals of the accelerometer regarding the respiration.

* * * * *